United States Patent [19]

Palumbo

[11] Patent Number: 5,087,506
[45] Date of Patent: Feb. 11, 1992

[54] ABSORBENT ELEMENT AND AN ABSORBENT ARTICLE INCLUDING THE ELEMENT

[75] Inventor: Gianfranco Palumbo, Pescara, Italy

[73] Assignee: Faricerca S.p.A., Pescara, Italy

[21] Appl. No.: 494,355

[22] Filed: Mar. 16, 1990

[30] Foreign Application Priority Data

Mar. 16, 1989 [IT] Italy .............................. 67188 A/89

[51] Int. Cl.$^5$ ........................................... B32B 23/02
[52] U.S. Cl. .................................. 428/194; 428/192; 428/195; 428/212; 428/218; 428/284; 428/323; 428/327; 604/367; 604/368
[58] Field of Search ............... 428/192, 194, 195, 283, 428/284, 286, 323, 327, 913, 212, 218, 219, 220, 323; 604/367, 368

[56] References Cited

U.S. PATENT DOCUMENTS

| | | | |
|---|---|---|---|
| 4,212,302 | 7/1980 | Karami | 128/287 |
| 4,381,782 | 5/1983 | Mazurak et al. | 604/368 |
| 4,578,068 | 3/1986 | Kramer et al. | 604/368 |
| 4,631,227 | 12/1986 | Nakamura | 428/283 |
| 4,699,823 | 10/1987 | Kellenberger et al. | 428/218 |
| 4,755,178 | 7/1988 | Insley et al. | 428/283 |
| 4,822,668 | 4/1989 | Tanaka et al. | 428/283 |
| 4,994,037 | 2/1991 | Bernardin | 604/368 |
| 5,009,650 | 4/1991 | Bernardin | 604/368 |

FOREIGN PATENT DOCUMENTS

| | | |
|---|---|---|
| 108637 | 5/1986 | European Pat. Off. . |
| 210969 | 2/1987 | European Pat. Off. . |
| 212618 | 3/1987 | European Pat. Off. . |
| 217666 | 4/1987 | European Pat. Off. . |

*Primary Examiner*—James J. Bell
*Attorney, Agent, or Firm*—Sughrue, Mion, Zinn, Macpeak & Seas

[57] ABSTRACT

An absorbent element for disposable absorbent articles composed of hydrophilic fibres and a discontinuous layer of particles of a hydrogelling absorbent material disposed on the upper surface of the element including two side regions situates at least in correspondence with the central part of the element, in which the hydrogelling absorbent material is distributed at a greater concentration on the surface or within the element. When the absorbent element is used as an absorbent pad for disposable diapers, the two side regions are situated at least in the crutch region of the diaper so as to ensure more effective lateral leak-proofing.

22 Claims, 6 Drawing Sheets

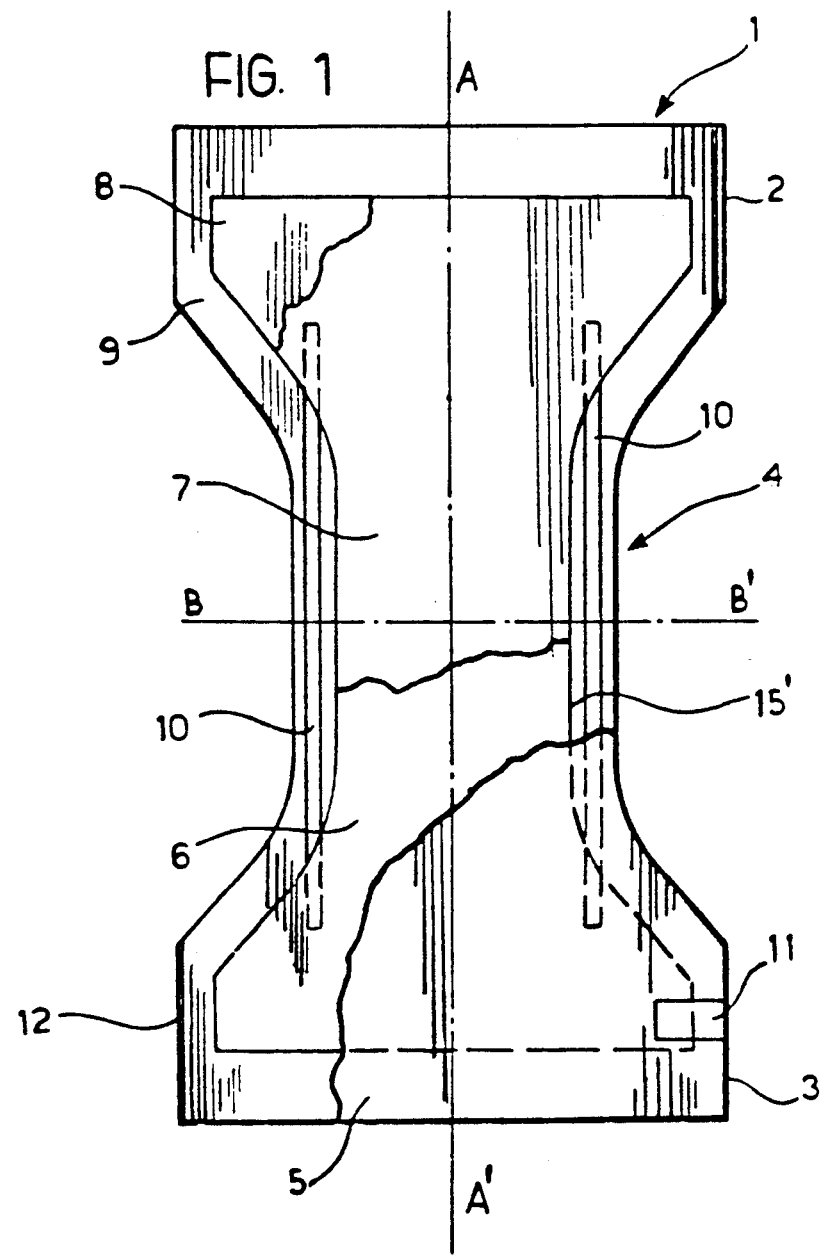
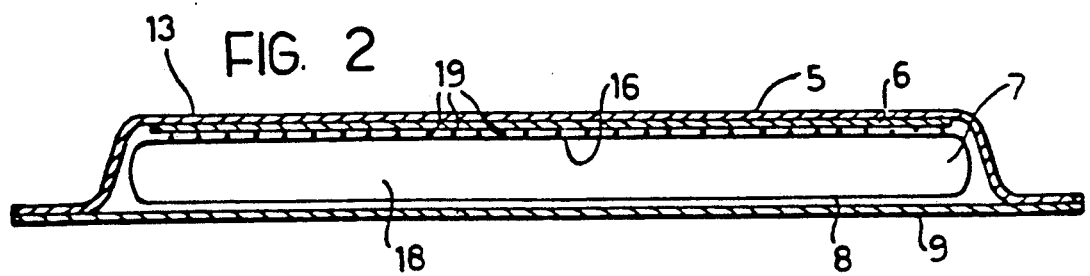

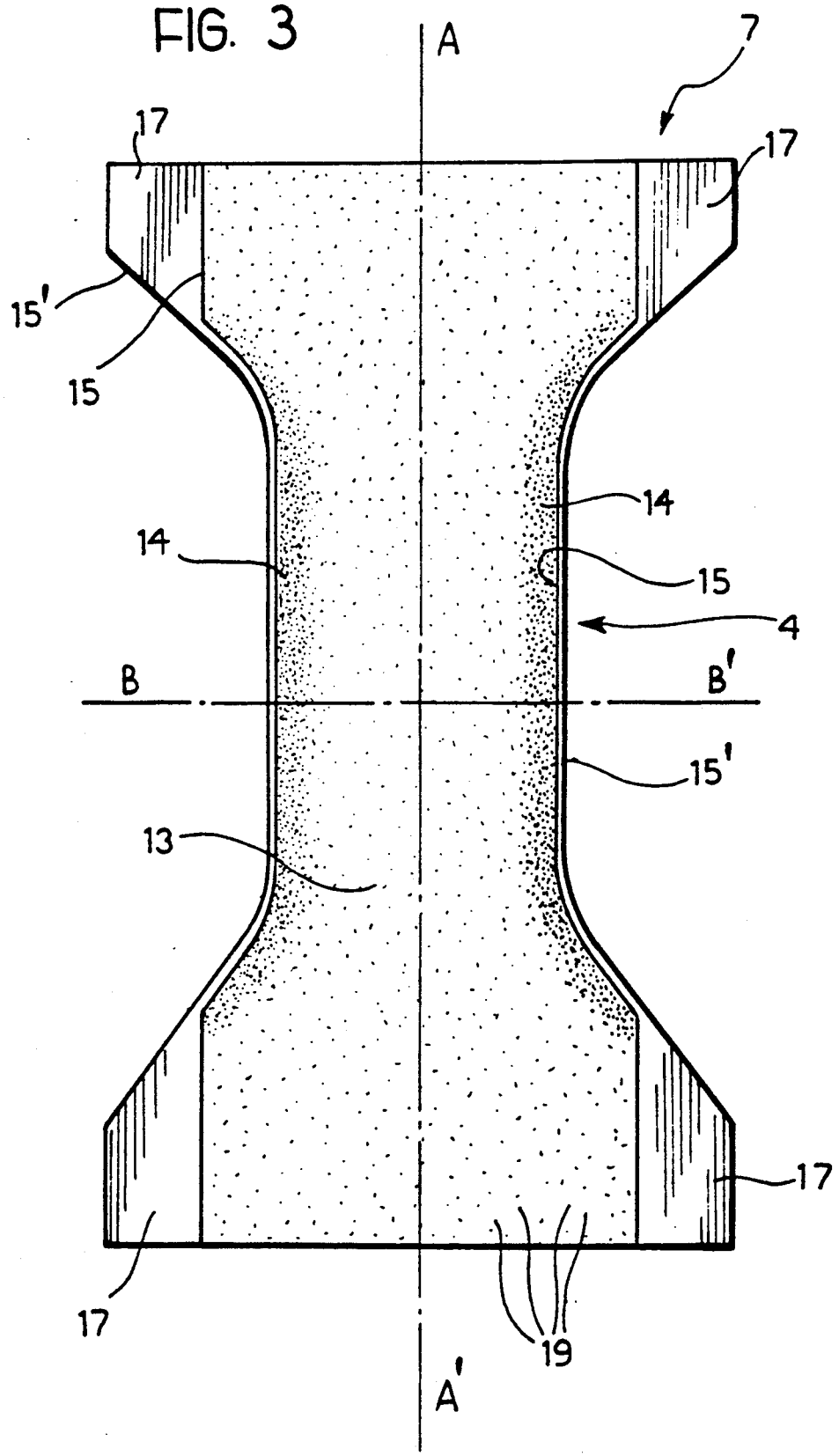

ABSORBENT ELEMENT AND AN ABSORBENT ARTICLE INCLUDING THE ELEMENT

FIELD OF THE INVENTION

The present invention relates to an absorbent element which is made from hydrophilic fibres, for example cellulose fibres, and may have a discontinuous layer of particles of a hydrogelling absorbent material on its surface which faces the user, the element being characterised by the presence along its longitudinal edges of regions extending at least along a central portion of the element, in which the hydrogelling absorbent material is distributed at a greater concentration than in the aforementioned layer so as to provide improved lateral leak-proofing.

DESCRIPTION OF THE PRIOR ART

Disposable absorbent articles such as babies' diapers, pads for incontinent adults, sanitary towels and similar products are well known and all are provided with absorbent elements for absorbing and retaining body fluids.

Such absorbent elements, commonly known as pads, must be able to take up the liquid quickly and distribute it internally so as to prevent leakage from the edges; moreover, they must have a good capacity for retaining the fluids when subjected to the normal pressures of use.

Absorbent pads made of cellulose fibres derived from conifer wood have satisfactory characteristics as regards their liquid-absorption rate and are therefore able effectively to distribute the liquid within them, but are much less effective from the point of view of retention and may allow the liquid to flow back or to leak from the sides of the absorbent structure under the normal pressures of use.

One way of avoiding this problem may be to increase considerably the quantity of absorbent material in the pad so that the flowing back and lateral leakage of liquid does not occur under the normal pressures of use; however, the very hydrophilic nature of cellulose and its absorption mechanism means that the absorbent surface of the pad tends to remain damp in any case and can thus cause the user to feel wet.

One attempt to resolve the problem of the flowing back and lateral leakage of liquid has been to mix particles of a hydrogelling absorbent material with the cellulose to increase the absorption and retention capacities of the absorbent element.

Hydrogelling materials, commonly known as superabsorbents, are polymers which can swell up and absorb large quantities of liquid, particularly water and, to a lesser extent, also body fluids.

They also have the particular property that they retain these fluids even under moderate pressure; because of these characteristics, their use in disposable absorbent articles has been proposed for some time.

Their good absorption capacity, however, is not matched by an equally good absorption rate and this can adversely affect the performance of absorbent articles incorporating these substances.

In fact, superabsorbents can give rise to a phenomenon known in the prior art as "gel blocking": when a superabsorbent particle comes into contact with the liquid, its outer surface starts to absorb the liquid and swells up, preventing the liquid from passing into the particle; the liquid can only penetrate further into the still-dry core of the particle by a very slow diffusion mechanism.

This phenomenon can prevent full use from being made of the large absorption capacities of superabsorbent substances and, in structures with mixed superabsorbents, may also involve a decrease in the absorption rate and consequently a greater chance of lateral leakage.

In these structures, there is therefore a marked decrease in the rate at which the liquid spreads into the absorbent pad.

Finally, although superabsorbent substances have the advantage compared with cellulose fibres that they retain absorbed liquids securely, the use of these substances simply mixed with cellulose fibres presents problems.

One of the many examples of absorbent structures constituted by mixtures of superabsorbents and cellulose fibres is provided by the patent application EP-A-122 042 which proposes a very dense absorbent structure in an attempt to resolve the aforementioned problem.

The patent application EP-A-O 254 476 proposes a low-density region positioned in the absorbent pad so as to receive the liquid directly when it is released; this region constitutes a kind of temporary storage sump for the liquid which must then be absorbed into the denser surrounding regions of the pad.

A substantially different approach to the solution of the problem of liquid flow-back from that based on the use of superabsorbent mixtures is offered in U.S. Pat. No. 3,888,256.

In this patent, the superabsorbent is situated only on the upper surface of a conventional pad; the quantity used is such that, as the particles absorb and swell up, they copenetrate each other to form a continuous layer which prevents the liquid from flowing back under normal conditions of use; however, this continuous layer also obstructs the absorption of any further quantities of liquid which may be released subsequently by the user and thus does not in itself represent an effective solution to the problem of lateral leakage.

A solution which aims to avoid the problems described is proposed in the present Applicant's European patent application No. 89830509.9, in which an absorbent element made of normal hydrophilic cellulose fibres has a discontinuous layer of hydrogelling absorbent material on its upper surface facing the user's body and, even when wet, this does not form a continuous impermeable layer such as to prevent the further penetration of liquid into the absorbent pad.

Although this solution has been shown to be effective in providing an improved feeling of dryness, particularly in versions which are different according to the sex of the user, there is still a problem in improving fluid retention, particularly with respect to leakage from the sides of the pad.

OBJECTS AND SUMMARY OF THE INVENTION

The main object of the present invention is to improve the lateral leak-proofing of absorbent elements for use in disposable absorbent articles. According to the present invention, this object is achieved by virtue of an absorbent element having the characteristics recited more specifically in the claims which follow. A further subject of the invention is an absorbent article including such an element.

In summary, the invention relates to an improved absorbent element having along its side edges regions extending along the whole of the side edge or along only a central portion thereof, where a high concentration of hydrogelling absorbent material is incorporated or distributed on the surface.

The two lateral regions are effective in reducing the lateral leakage of liquid.

DETAILED DESCRIPTION OF THE INVENTION

Further characteristics and advantages of the invention will become clear from the description which follows, given purely by way of illustrative but non-limiting, example, with reference to the appended drawings, in which:

FIG. 1 is a plan view of a disposable diaper using an absorbent element according to the present invention;

FIG. 2 is a sectional view of the diaper taken on the longitudinal axis A—A' of FIG. 1;

FIG. 3 is a plan view of an absorbent element according to the present invention;

Figure 4:
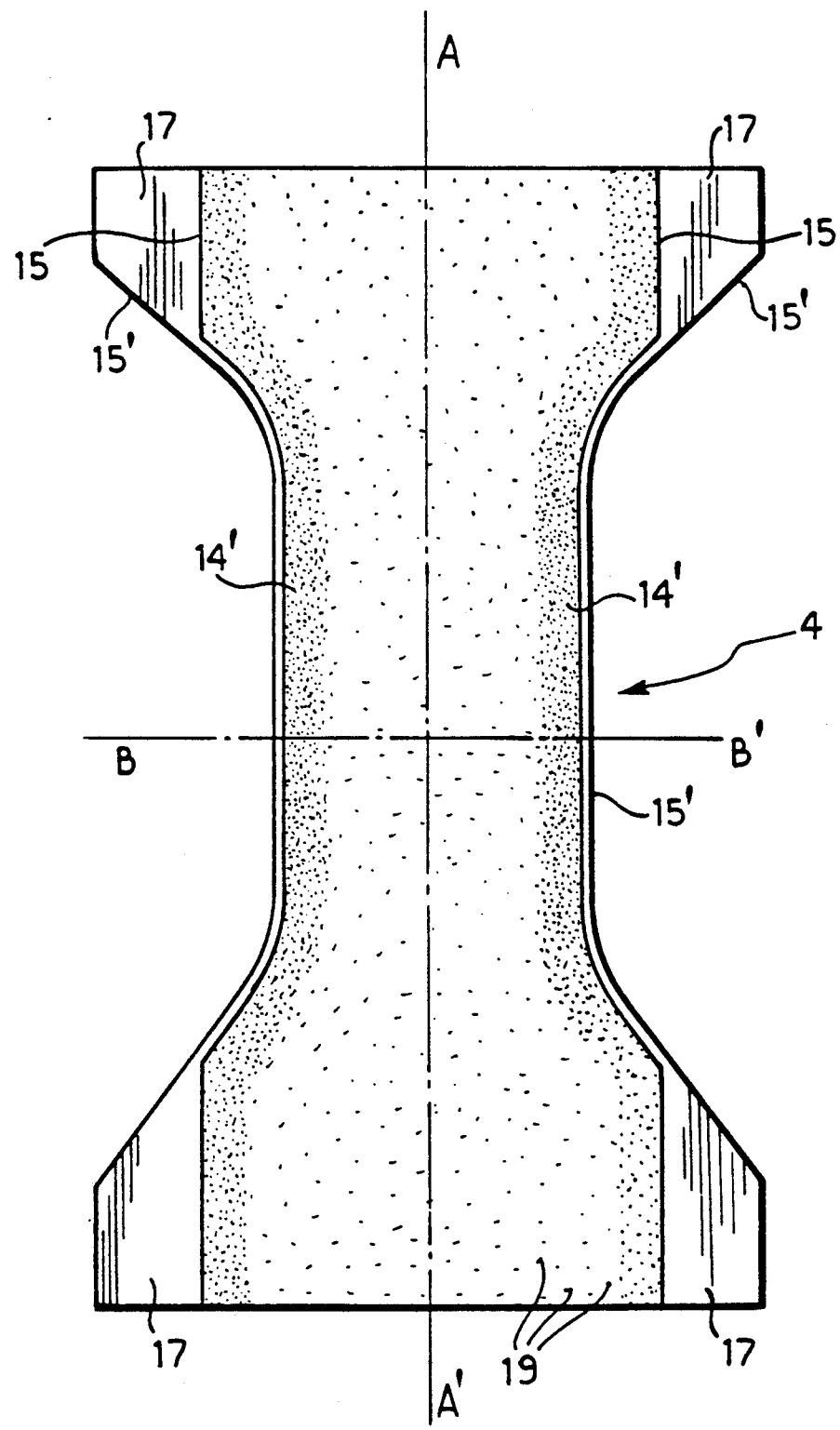
FIG. 4 is a plan view of a different configuration of the absorbent element according to the present invention.

The absorbent elements of the present invention will be described with reference to their use in disposable absorbent articles; these articles are worn by the user in direct contact with the body to absorb body fluids, and are then thrown away after a single use.

The disposable diaper shown in FIG. 1 represents a preferred embodiment of an absorbent article according to the present invention, but the present invention is intended also to be applicable to other disposable absorbent articles, such as articles for the incontinent, sanitary towels and the like.

FIG. 1 is a plan view of a diaper (1) in an extended configuration with some portions of its structure sectioned to show more clearly the construction of the diaper; in particular, the side of the diaper which comes directly into contact with the user is shown.

FIG. 1 shows two end regions, a front end region 2 and a rear end region 3, which in use are positioned in correspondence with the user's waist, and a central region 4 which is situated between them and is positioned around the crutch region; a longitudinal axis AA' and a transverse axis BB' are also shown.

The diaper comprises an upper layer 5 of non-woven fabric which is permeable to liquids and is intended to come directly into contact with the user's skin, a layer 6 of tissue which is preferably wet-strength, immediately beneath the non-woven fabric, an absorbent element 7 according to the present invention and described further below, a second layer 8 of tissue which is preferably wet-strength, an impermeable plastics sheet 9, and elastic elements 10 positioned on both sides of the absorbent element 7 for effecting a seal around the user's legs in use; one of the two adhesive tabs 11 commonly used for fixing the diaper 1 around the user's waist is also visible on the rear region 3.

The sheet of non-woven fabric and the plastics sheet 9 are of the same shape and size and correspond to the outline 12 of the whole diaper, whilst the two layers of tissue 6 and 8 are shaped like the absorbent element 7 situated between them.

Figure 5:
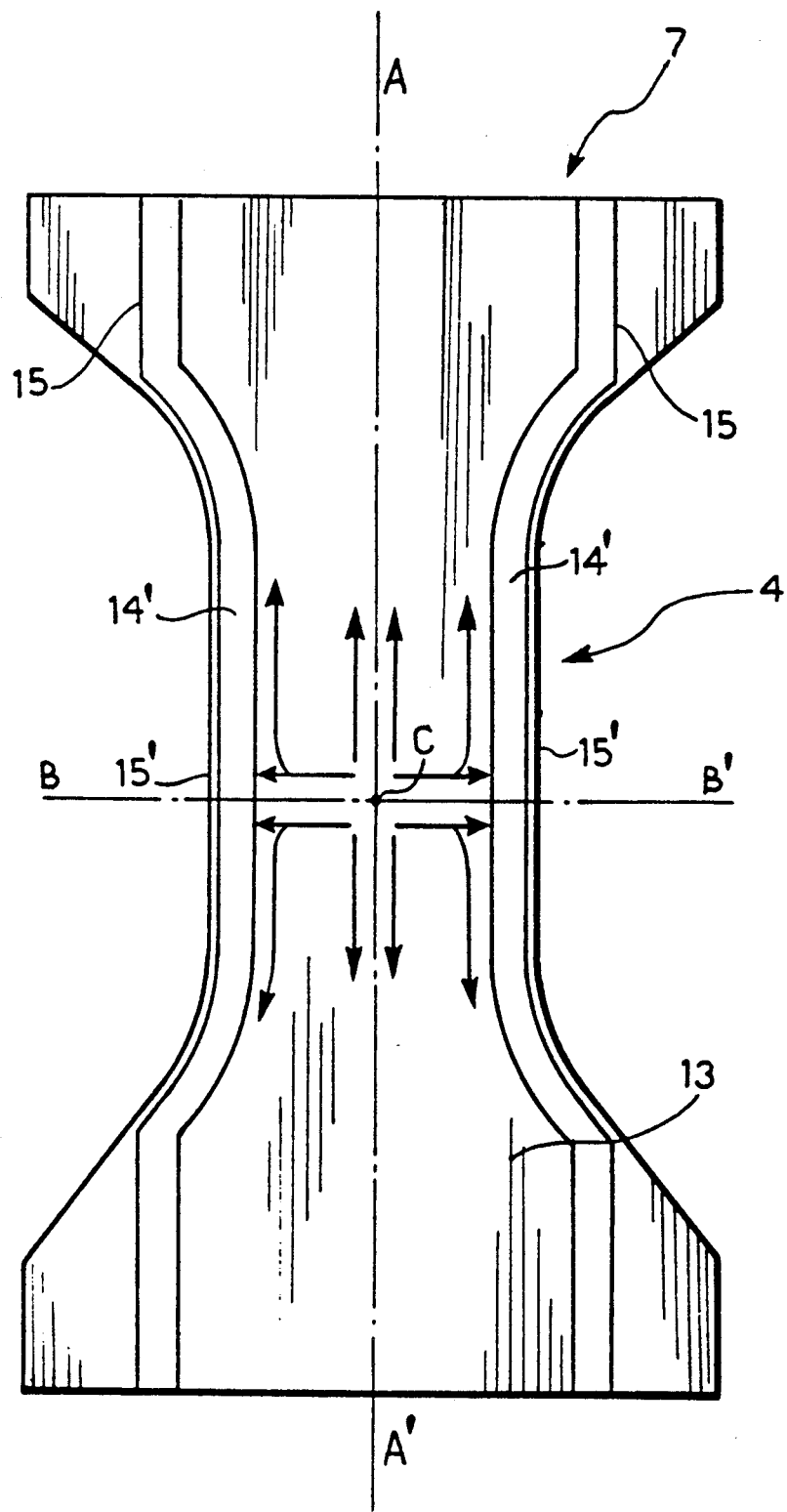
FIG. 5 is a plan view of an absorbent element according to the present invention, showing the element during the absorption of a certain quantity of liquid.

In the configuration shown, the absorbent element 7 has a conventional hourglass-shape, as can better be seen in FIGS. 3, 4 and 5 where it is shown on its own; in particular, FIGS. 3 and 4 shown a main portion 13 of the pad which is affected by the surface distribution and/or the mixing therein of the superabsorbent, and includes two side regions 14 and 14' generally adjacent the longitudinal edges 15 of the main portion 13 of the pad and extending at least in correspondence with its central region 4.

The main portion 13 does not necessarily include the entire upper surface 16 of the pad but may exclude larger or smaller parts of the so-called ears of the pad; the main portion 13 affected by the surface distribution and/or the mixing therein of the superabsorbent does not include the four end regions 17 of the ears in any of the cases shown; the longitudinal edges 15 of the main portion 13 of the pad may not therefore coincide with the longitudinal edges 15' of the pad, at least in correspondence with the four end regions 17, since they are situated inwardly thereof.

The absorbent element 7 is made solely of hydrophilic fibres 18, such as, for example, cellulose fibres derived from conifer wood pulp.

FIG. 2 shows that particles 19 of hydrogelling absorbent material can be distributed on the upper surface of the absorbent element 7; the surface distribution involves the main portion 13 of the pad, as distinct from the two lateral regions 14 and 14', and is non-continuous.

Suitable hydrogelling absorbent materials may be inorganic or organic materials, such as cross-linked polymers wholly known in the art; preferably, the superabsorbent produced by Chemische Fabrik Stockhausen under the trade name Favor Sab 922 is used.

The average size of the particles 19, that is, the weighted average of the smallest dimensions of the individual particles, may be between 100 and 800 microns, preferably between 200 and 500 microns.

The surface distribution of the superabsorbent particles 19 on the main portion 13 of the pad, as distinct from the side regions 14 or 14' when it is present, must be non-continuous, that is, such as to ensure that the particles are substantially isolated from each other before the absorption of liquid and that they remain so even after the swelling which results from the absorption, or at any rate that they do not form a continuous layer on the surface of the pad when they swell up.

In general, such a result is achieved by a surface distribution of particles 19 of the preferred dimensions at concentrations of between 5 g/m² and 70 g/m², preferably between 10 g/m² and 60 g/m². In order to improve the performance of the absorbent element 7 of the present invention, particularly with regard to its behaviour in relation to the lateral leakage of liquid, the side regions 14 and 14' of the main portion 13 of the pad are characterized by the presence of hydrogelling absorbent material distributed at a higher concentration.

FIG. 3 shows a preferred configuration of this distribution; one can see therein the main portion 13 of the pad 7, including the two side regions 14 extending along the longitudinal edges 15 of the main portion 13 of the pad in correspondence with the central region 4; the superabsorbent is distributed in these side regions 14, on the surface or mixed with the cellulose fibres, at concentrations of between 100 g/m² and 300 g/m², preferably between 150 g/m² and 250 g/m², whilst the main portion 13, as distinct from the two side regions (14), preferably has a discontinuous surface distribution of the superabsorbent.

Each side region 14 with a high concentration of hydrogelling absorbent material is generally between 5 mm and 20 mm wide.

The superabsorbent distributed in correspondence with the two side regions 14 may be of the same type as any used on the rest of the surface of the main portion 13 of the pad, or may be different.

FIG. 4 shows an alternative but substantially equivalent configuration to that just described; the only difference is in the positioning of the two side regions 14 with high concentrations of superabsorbent which, in this case, extend over the entire length of each longitudinal edge 15 of the main portion 13 of the pad instead of being limited to the central region 4 which corresponds to the crutch.

Surprisingly, it has been found that these high concentrations of superabsorbent along the side regions 14 and 14' of the pad bring considerable advantages in use, particularly for preventing lateral leakages of liquid.

Such high concentrations, particularly when they are associated with the mixing of the superabsorbent particles with the hydrophilic fibres, represent an apparent contradiction of what has been found hitherto in the prior-art attempts to resolve the problem of "gel blocking".

Although this phenomenon is not yet completely understood, in practice, it results in a slower rate of spread of the fluids into the pads containing hydrogelling materials, as explained above.

Without wishing to be bound to any particular theory, one may assume that the improved behaviour with regard to lateral leakages of liquid exhibited by the pads according to the present invention is actually due to the "gel blocking" phenomenon taking place in the side regions 14 or 14' with high concentrations of superabsorbent; in these regions, the high concentration of hydrogelling absorbent material slows the spread of liquid in a transverse direction towards the side edges 15 of the main portion 13 of the pad 7.

FIG. 5 shows an absorbent element 7 according to the present invention during the absorption of a certain quantity of liquid released in correspondence with the centre C of the element.

The liquid spreads in all directions from the deposition zone C, as indicated by the thick arrows, and reaches the two side regions 14' with high concentrations of hydrogelling absorbent material which, in this case, extend over the entire length of each longitudinal edge 15 of the main portion 13 of the pad; at this point, the superabsorbent swells up and, apparently because of the establishment of "gel blocking" due to the high concentration, forms a barrier to the further transverse spread of the liquid towards the longitudinal edges 15 of the main portion 13 of the pad.

Any liquid which continues to reach the side regions 14' of high concentration has a preferential tendency to spread parallel thereto in a longitudinal direction, thus affecting regions of the pad which are not yet wet, as shown by the thinner arrows.

It is also possible that the swelling of the superabsorbent material in the two regions 14 or 14' contributes to the limiting of lateral leakages of liquid but it is considered that the predominant contribution should be attributed to the first effect described.

It can therefore be said that the improved performance obtained with the absorbent element according to the present invention can be attributed to the fact that advantage is taken of a phenomenon such as "gel blocking" which, in the prior art, was considered a disadvantage.

Figure 6:
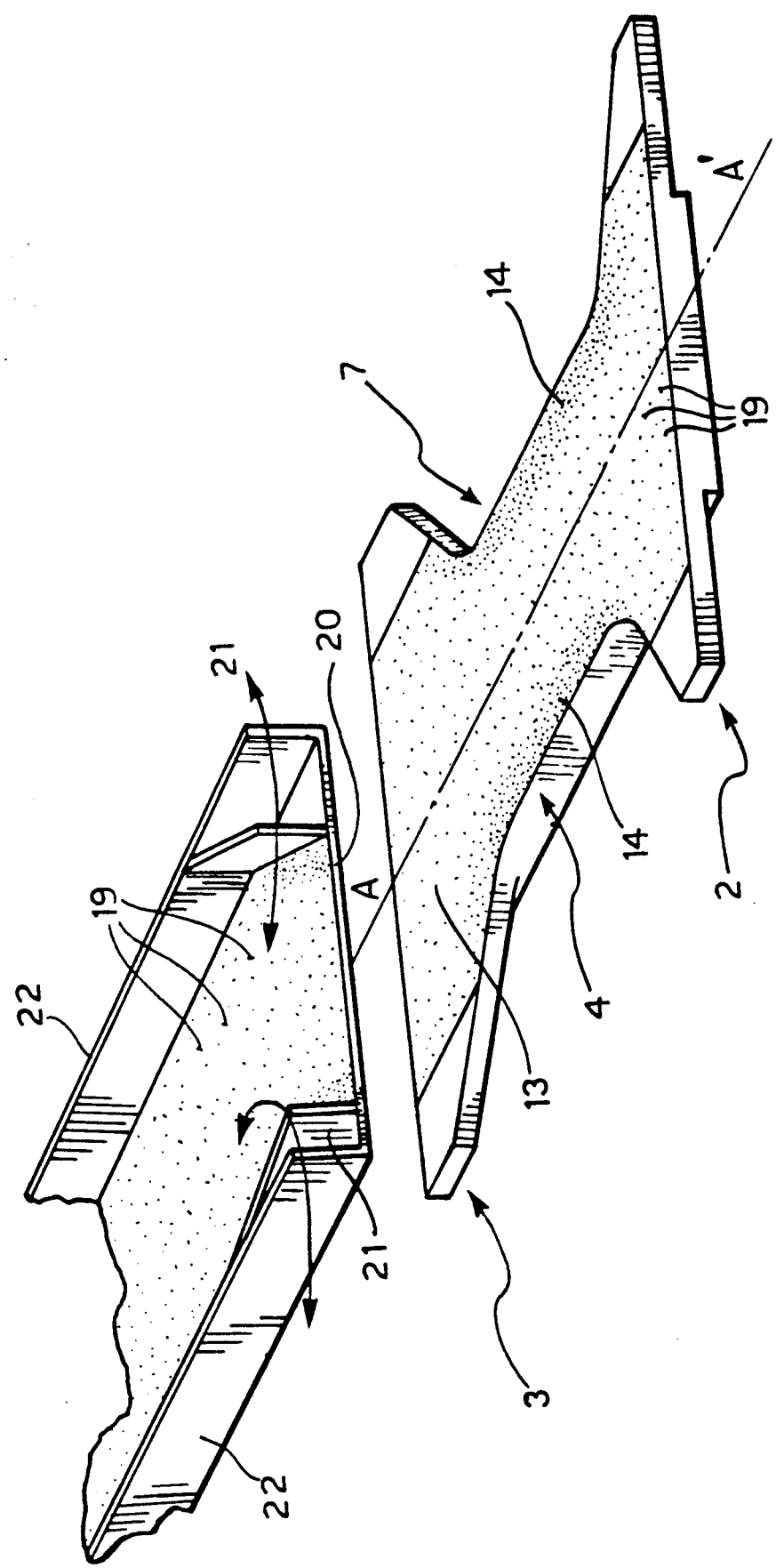
FIG. 6 is a perspective view of an absorbent element according to the present invention and of part of a device for producing the absorbent element.

FIG. 6 shows part of the device for producing an absorbent element according to the present invention, particularly in the configuration shown in FIG. 3; the chute 20 distributes the hydrogelling material 19 on the main portion 13 of the upper surface 16 of the pad at a high concentration equal to the preferred value in the two side regions 14 which, in this case, extend along the central region 4 of the pad, and at a constant concentration equal to the preferred value on the rest of the main region 13.

The two blades 21 hinged to the sides 22 of the chute can pivot in the two senses indicated by the arrows: FIG. 4 shows the position of maximum deflection towards the centre of the chute, corresponding to the greatest concentration of superabsorbent towards the two side regions 14; when the blades 21 are oriented parallel to the sides 22, however, the chute 20 distributes the superabsorbent uniformly and discontinuously over the whole width of the main portion (13) of the pad 7, as occurs in correspondence with the front (2) and rear (3) regions which do not have side regions with high concentrations.

Figure 7:
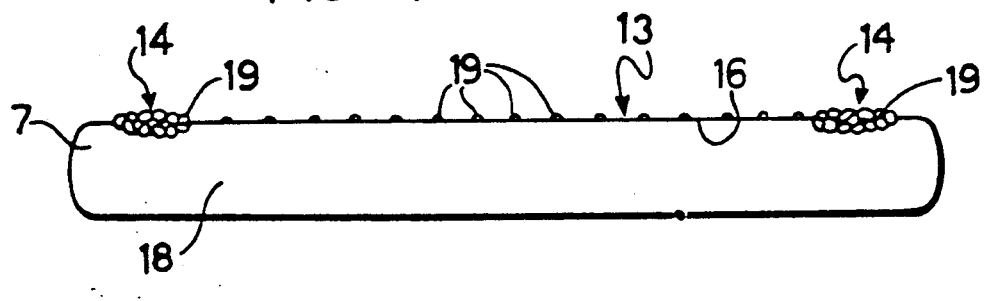
FIG. 7 is a section of the absorbent element alone, taken on the axis BB' of FIG. 1 and showing the regions with high concentrations of hydrogelling absorbent material situated on the surface of the element.
Figure 8:
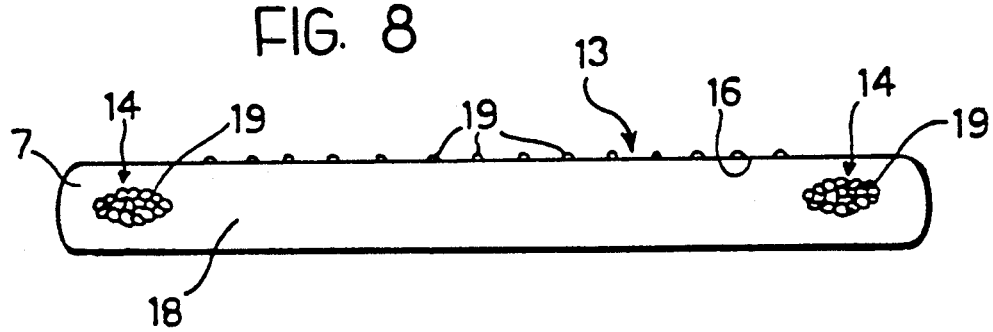
FIG. 8 is a section of the absorbent element alone, taken on the axis BB' of FIG. 1 and showing the regions which have high concentrations of hydrogelling absorbent material situated within the element.

FIGS. 7 and 8 are sectional views of the pad 7 of the present invention alone, taken along the transverse axis BB' of FIG. 1; in FIG. 7, the two side regions 14 or 14' have the preferred concentration of superabsorbent 19 distributed on the surface 16 of the pad, whilst FIG. 8 shows the two side regions 14 or 14' formed with the preferred concentration of superabsorbent 19 mixed with the hydrophilic fibres (18)

Figure 9:
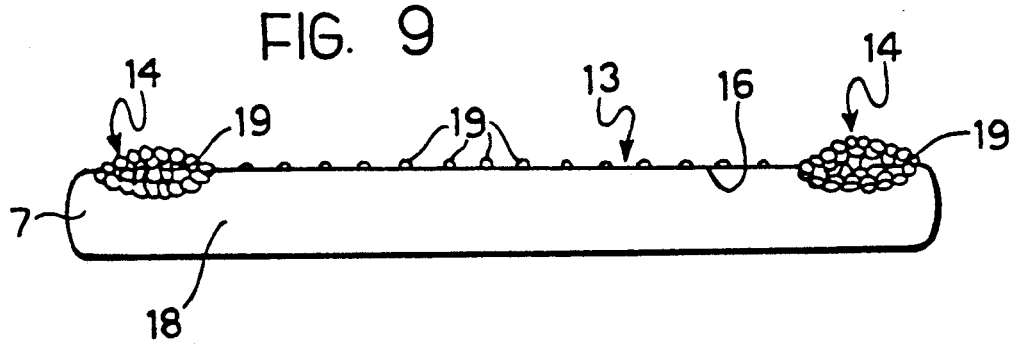
FIG. 9 is a section similar to that of FIG. 7, showing the regions with high concentrations of hydrogelling absorbent material in the configuration of use.
Figure 10:
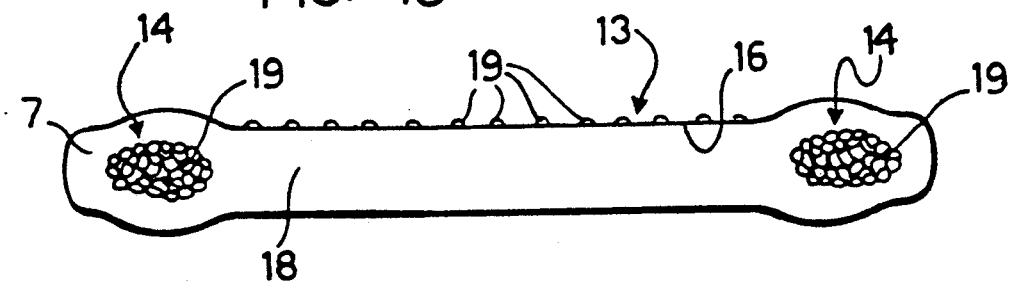
FIG. 10 is a section similar to that of FIG. 8, showing the regions with high concentrations of hydrogelling absorbent material in the configuration of use.

FIGS. 9 and 10 are two sectional views the same as FIGS. 7 and 8, showing the appearance of the superabsorbent 19 after the absorption of a certain quantity of liquid; the amount of swollen superabsorbent 19 in correspondence with the two regions 14 and 14' can slow the spread of liquid towards the side edges of the pad, as already described, by virtue of the establishment of the "gel blocking" phenomenon.

These four drawings also show the superabsorbent particles 19 discontinuously distributed in the preferred concentration on the main portion 13 of the upper surface 16 of the pad, as distinct from the two side regions 14 or 14'.

A diaper including an absorbent element formed according to the present invention will be described by way of non-limiting example.

The liquid-permeable upper layer is a spunbounded non-woven fabric made of hydrophobic polypropylene yarn, with a thickness of approximately 0.180 mm and a weight of approximately 23.00 g/m$^2$.

The intermediate layers situated between the non-woven fabric and the absorbent element and, lower down, between that element and the plastics sheet are made of a wet-strength tissue approximately 0.080 mm thick and weighing approximately 18.00 g/m$^2$; the plastics sheet is an impermeable polyethylene film about 0.025 mm thick and weighing about 24.30 g/m$^2$.

The hourglass-shaped absorbent element is made of cellulose fibres with an average density of approximately 10 cm$^3$/g; the pad is 460 mm long and 290 mm wide in correspondence with the front and rear ends and 135 mm wide in correspondence with the central region; the total weight of cellulose is 56 g.

The main portion of the upper surface of the pad on which the superabsorbent is distributed is rectangular in this case, with a length equal to the length of the pad and a width equal to the smallest width of the pad; in other words, the main portion completely excludes the four ear regions.

The two side regions with high concentrations of superabsorbent are 15 mm wide and extend for a total distance of 200 mm in correspondence with the central region of the pad which, in use, is situated in the crutch region.

The superabsorbent is constituted by granules of the aforementioned Favor Sab 922 with average dimensions of between 200 and 500 microns; it is distributed on the surfaces of the two side regions of high concentrations and also on the rest of the main portion.

The concentrations used are approximately 185 g/m$^2$ for the side regions and approximately 30 g/m$^2$ for the rest of the main portion.

In a different embodiment which is simpler to produce, the two side regions with high concentrations may extend over the entire length of each straight longitudinal edge of the main portion of the pad; in this case, for the same overall shape and dimensions of the pad, the side regions are about 10 mm wide and their lengths are obviously equal to that of the whole pad.

If the overall quantity of superabsorbent used remains constant, the concentration falls to about 120 g/m$^2$ in the two side regions whilst its value increases only slightly to approximately 32 g/m$^2$ for the rest of the main portion.

In use, both the diapers have shown good behaviour from the point of view of the retention of fluids, particularly as regards leakages from the sides of the pad.

What is claimed is:

1. An absorbent element made from hydrophilic fibres comprising in combination:
a discontinuous layer of hydrogelling absorbent material distributed at a concentration between 5 g/m$^2$ and 70 g/m$^2$ on an upper surface thereof facing the user, and a region along each of laterally opposed longitudinal edges having a high concentration of hydrogelling absorbent material distributed at a concentration of between 100 g/m$^2$ and 300 g/m$^2$.

2. An absorbent element according to claim 1, wherein the concentration of the hydrogelling absorbent element distributed in the said regions is between 150 g/m$^2$ and 250 g/m$^2$.

3. An absorbent element according to claim 1, wherein each of the said regions is situated in correspondence with a central portion of the respective longitudinal edge.

4. An absorbent element according to claim 2, wherein each of the said regions extends along the entire length of the respective longitudinal edge.

5. An absorbent element according to claim 1, wherein the hydrogelling absorbent material is distributed on the surface of the element in each of the said regions.

6. An absorbent element according to claim 1, wherein the hydrogelling absorbent material is mixed with the hydrophilic fibres of the absorbent element in each of the said regions.

7. An absorbent element according to claim 1, wherein each of the said regions is between 5 mm and 20 mm wide.

8. An absorbent element according to claim 1, wherein the absorbent element has a discontinuous layer of hydrogelling absorbent material distributed at a concentration of between 10 g/m$^2$ and 60 g/m$^2$ on its upper surface which faces the user, as distinct from each of the said regions.

9. An absorbent element according to claim 1, wherein the hydrogelling absorbent material is a polyacrylate.

10. An absorbent element according to claim 1, wherein the hydrogelling absorbent material is in the form of particles with average dimensions of between 100 microns and 800 microns.

11. An absorbent element according to claim 1, wherein the hydrogelling absorbent material is in the form of particles with average dimensions of between 200 microns and 500 microns.

12. An absorbent article including a lower impermeable plastics sheet, an upper permeable non-woven sheet textile, and an absorbent element between the plastics sheet and the non-woven sheet, wherein the absorbent element is made from hydrophilic fibres and has longitudinal edges, and wherein a discontinuous layer of hydrogelling absorbent material distributed at a concentration of between 5 g/m$^2$ and 70 g/m$^2$ is on the upper surface of the absorbent element which faces the user, and a region along each of said longitudinal edges wherein a high concentration of hydrogelling absorbent material is distributed at a concentration of between 100 g/m$^2$ and 300 g/m$^2$.

13. An absorbent element according to claim 12, wherein the concentration of the hydrogelling absorbent element distributed in the said regions is between 150 g/m$^2$ and 250 g/m$^2$.

14. An absorbent article according to claim 12, wherein each of the said regions is situated in correspondence with a central portion of the respective longitudinal edge.

15. An absorbent article according to claim 12, wherein each of the said regions extends along the entire length of the respective longitudinal edge.

16. An absorbent article according to claim 12, wherein the hydrogelling absorbent material is distributed on the surface of the element in each of the said regions.

17. An absorbent article according to claim 12, wherein the hydrogelling absorbent material is mixed with the hydrophilic fibres of the absorbent element in each of the said regions.

18. An absorbent article according to claim 12, wherein each of the regions is between 5 mm and 20 mm wide.

19. An absorbent article according to claim 12, wherein the absorbent element has a discontinuous layer of hydrogelling absorbent material distributed at a concentration of between 10 g/m$^2$ and 60 g/m$^2$ on its upper surface which faces the user, as distinct from each of the said regions.

20. An absorbent article according to claim 12, wherein the hydrogelling absorbent material is a polyacrylate.

21. An absorbent article according to claim 12, wherein the hydrogelling absorbent material is in the form of particles with average dimensions of between 100 microns and 800 microns.

22. An absorbent article according to claim 12, wherein the hydrogelling absorbent material is in the form of particles with average dimensions of between 200 microns and 500 microns.

* * * * *